US006306600B1

(12) United States Patent
Kain et al.

(10) Patent No.: US 6,306,600 B1
(45) Date of Patent: Oct. 23, 2001

(54) RAPIDLY DEGRADING GFP-FUSION PROTEINS AND METHODS OF USE

(75) Inventors: Steve Kain, Belmont; Xianqiang Li, Palo Alto, both of CA (US)

(73) Assignee: Clontech Laboratories, Inc., Palo Alto, CA (US)

(*) Notice: Subject to any disclaimer, the term of this patent is extended or adjusted under 35 U.S.C. 154(b) by 0 days.

(21) Appl. No.: 09/364,946

(22) Filed: Jul. 30, 1999

Related U.S. Application Data

(60) Division of application No. 09/191,233, filed on Nov. 13, 1998, which is a continuation-in-part of application No. 09/062,102, filed on Apr. 17, 1998, now Pat. No. 6,130,313.

(51) Int. Cl.⁷ ............................. C12Q 1/68; C12P 21/04; C12N 15/00; C12N 15/09; C12N 15/63

(52) U.S. Cl. ..................... 435/6; 435/70.1; 435/320.1; 435/325; 435/69.1; 435/455; 530/350; 530/324; 536/23.4; 536/23.5

(58) Field of Search .................... 435/670.1, 320.1, 435/325, 69.1, 455; 530/324, 350; 536/23.5, 23.4

(56) References Cited

PUBLICATIONS

Rechsteiner et al., Cell Biology, vol. 1, pp. 435–440, 1990.*
Loetscher et al., The Journal of Biological Chemistry, vol. 266, No. 17, pp. 11213–11220, 1991.*
Li et al., The Journal of Biological Chemistry, vol. 273, No. 52, pp. 34970–34975, Dec. 25, 1998.*
Moradpour et al., Characterization of Cell Lines Allowing Tightly Regulated Expression of Hepatitis C Virus Core Protein, Virology vol 222, p. 51–63, 1996.*

* cited by examiner

*Primary Examiner*—Anthony C. Caputa
*Assistant Examiner*—Jennifer Hunt
(74) *Attorney, Agent, or Firm*—Bret E. Field; Bozicevic, Field & Francis LLP

(57) ABSTRACT

Green fluorescent protein (GFP) is widely used as a reporter in determining gene expression and protein localization. The present invention provides fusion proteins with a half life of ten hours or less with several embodiments having half lives of 4 hours or less. Such proteins may be constructed by fusing C-terminal amino acids of the degradation domain of mouse ornithine decarboxylase (MODC), which contains a PEST sequence, to the C-terminal end of an enhanced variant of GFP (EGFP). Fluorescence intensity of the fusion protein in transfected cells is similar to that of EGFP, but the fusion protein, unlike EGFP, is unstable in the presence of cycloheximide. Specific mutations in the MODC region have resulted in mutants with varying half lives, useful for a variety of purposes.

9 Claims, 12 Drawing Sheets

FIG. 6

MODC₄₂₂₋₄₆₁

PEST Sequence

```
                        423                                    450
EGFP-MODC₄₂₂₋₄₆₁     --HGFPPEVEEQDDGTLPMSCAQESGMDRH--  (SEQ ID NO. 3)
P426A/P427A          -----AA-------------------------
P438A                ----------------A---------------
E428A/E430A/E431A    ------A-AA----------------------
E44A                 ----------------------A---------
S440A                ------------------A-------------
S445A                ------------------------A-------
T436A                --------------A-----------------
D433A/D434A          -----------AA-------------------
D448A                ---------------------------A----
H423A                A-------------------------------
R449A/H450A          ----------------------------AA--
```

FIG. 7

Table 1. FACS analysis of EGFP, EGFP-MODC $_{422-461}$, and mutations in transfected CHO K1 Tet-off cells.

| Constructs | 0h | (initial) | 2h | 4h |
|---|---|---|---|---|
| EGFP | 100% | (63.6) | 107% | 92% |
| EGFP-MODC $_{422-461}$ | 100% | (12.6) | 52% | 29% |
| P426A/P427A | 100% | (11.5) | 39% | 11% |
| P438A | 100% | (34.1) | 79% | 60% |
| E428A/E430A/E431A | 100% | (17.3) | 20% | 15% |
| E444A | 100% | (12.6) | 69% | 65% |
| S440A | 100% | (21.6) | 78% | 66% |
| S445A | 100% | (23.5) | 29% | 20% |
| T436A | 100% | (46.9) | 70% | 47% |
| D433A/D434A | 100% | (11.31) | 22% | 6% |
| D448A | 100% | (32.6) | 30% | 15% |
| H423A | 100% | (12.2) | 50% | 25% |
| R449A/H450A | 100% | (27.9) | 93% | 86% |

Transfection was performed in CHO/tTA cells using the procedure as described in Methods. After 24 hours, cells were treated with CHx for 0, 2 and 4 hours, and analyzed for fluorescence intensity by FACS Caliber (Becton Dickinson). The fluorescent cells at each time point are represented as a percentage of initial.

US 6,306,600 B1

RAPIDLY DEGRADING GFP-FUSION PROTEINS AND METHODS OF USE

CROSS-REFERENCE TO RELATED APPLICATION

This is a divisional application of U.S. Ser. No. 09/191,233 filed on Nov. 13, 1998, which is a continuation in part of U.S. patent application Ser. No. 09/062,102, filed Apr. 17, 1998, now U.S. Pat. No. 6,130,313.

BACKGROUND OF THE INVENTION

1. Field of the Invention

This invention relates to the field of biochemical assays and reagents. More specifically, this invention relates to modified fluorescent proteins and to methods for their use.

2. Description of the Related Art

Because of its easily detectable green fluorescence, green fluorescent protein (GFP) from the jellyfish *Aequorea Victoria* has been used widely to study gene expression and protein localization. GFP fluorescence does not require a substrate or cofactor; hence, it is possible to use this reporter in numerous species and in a wide variety of cells. GFP is a very stable protein which can accumulate and thus is often toxic to mammalian cells.

Recently, crystallographic structures of wild-type GFP and the mutant GFP S65T reveal that the GFP tertiary structure resembles a barrel (Ormo et al. (1996) *Science* 273: 1392–1395; Yang, F., Moss, L. G., and Phillips, G. N., Jr. (1996) *Nature Biotech* 14: 1246–1251). The barrel consists of beta sheets in a compact antiparallel structure. In the center of the barrel; an alpha helix containing the chromophore is shielded by the barrel. The compact structure makes GFP very stable under diverse and/or harsh conditions, such as protease treatment, making GFP an extremely useful reporter in general. On the other hand, its stability makes it difficult to determine short-term or repetitive events.

A great deal of research is being performed to improve the properties of GFP and to produce GFP reagents useful for a variety of research purposes. New versions of GFP have been developed via mutation, including a "humanized" GFP DNA, the protein product of which has increased synthesis in mammalian cells (see Cormack, et al., (1996) *Gene* 173, 33–38; Haas, et al., (1996) *Current Biology* 6, 315–324; and Yang, et al., (1996) *Nucleic Acids Research* 24, 4592–4593). One such humanized protein is "enhanced green fluorescent protein" (EGFP). Other mutations to GFP have resulted in blue-, cyan- and yellow-fluorescent light emitting versions.

Ornithine decarboxylase (ODC) is an enzyme critical in the biosynthesis of polyamines. Murine ornithine decarboxylase is one of most short-lived proteins in mammalian cells, with a half life of about 30 minutes (Ghoda, et al., (1989) *Science* 243, 1493–1495; and Ghoda, et al. (1992) *Mol. Cell. Biol.* 12, 2178–2185). Rapid degradation of murine ornithine decarboxylase has been determined to be due to the unique composition of its C-terminus, a portion of which has a PEST sequence—a sequence which has been proposed as characterizing short-lived proteins. The PEST sequence contains a region enriched with proline (P), glutamic acid (E), serine (S), and threonine (T), often flanked by basic amino acids, lysine, arginine, or histidine (Rogers, et al., (1989) *Science* 234:364–68; Reichsteiner, M. (1990) Seminars in *Cell Biology* 1:433–40).

The ornithine decarboxylase of Trypanosoma brucei (TbODC) does not have a PEST sequence, and is long-lived and quite stable when it is expressed in mammalian cells (Ghoda, et al. (1990) *J. Biol. Chem.* 265: 11823–11826); however appending the C terminus of murine ornithine decarboxylase to TbODC makes TbODC become unstable. Moreover, deletion of the C-terminal, PEST-containing region from murine ornithine decarboxylase prevents its rapid degradation (Ghoda, L., et al. (1989) *Science* 243: 1493–1495).

The prior art is deficient in a destabilized or short-lived GFP. The present invention fulfills this need in the art.

SUMMARY OF THE INVENTION

A rapid turnover or destabilized GFP can be used in research applications where prior art GFPs cannot. Such applications include using the destabilized GFP as a genetic reporter for analyzing transcriptional regulation and/or cis-acting regulatory elements, or as a tool for studying protein degradation. Further, a rapid turnover GFP permits easier development of stable cell lines which express the GFP gene, since toxic levels of GFP are avoided because the GFP protein is degraded quickly.

The present invention provides a fusion protein with a half life decreased markedly from that of wildtype GFP. In one embodiment, there is provided a fusion protein comprising an EGFP fused to a peptide producing a destabilized protein. In another embodiment, there is provided a fusion protein with a half life of about ten hours or less, preferably with a half life of about 4 hours or less, more preferably with a half life of 2 hours or less and even more preferably with a half life of 1 hour or less. A preferred embodiment of this aspect of the invention includes EGFP, and/or a PEST sequence-containing portion of a C-terminus of murine ornithine decarboxylase (MODC). Specific preferred embodiments of the present invention include EGFP-MODC$_{376-461}$; EGFP-MODC$_{376-456}$; EGFP-MODC$_{422-461}$; P426A/P427A; P438A; E428A/E430A/E431A; E444A; S440A; S445A; T436A; D433A/D434A; and D448A.

In yet another aspect of the invention, there is provided an isolated DNA molecule encoding a fluorescent fusion protein with a half life that is markedly decreased from that of wildtype GFP. In one embodiment of this aspect of the invention, there is provided a n isolated DNA molecule encoding a fluorescent fusion protein with a half life of about ten hours or less, preferably with a half life of about 4 hours or less, more preferably with a half life of 2 hours or less and even more preferably with a half life of 1 hour or less. In a preferred embodiment of this aspect of the invention, the isolated DNA molecule encoding the fluorescent fusion protein is a synthetic GFP gene containing codons preferentially found in highly expressed human proteins. Further, the present invention provides a vector capable of expressing the isolated DNA molecule encoding a GFP fusion protein with a decreased half life. In one embodiment of the vector, the vector contains an inducible promoter.

In another aspect of the invention, there is provided a method of labeling cells with a transient GFP reporter. In this method, a DNA vector comprising an inducible promoter and the isolated DNA encoding a GFP fusion protein with a decreased half life is utilized. This vector is transfected into cells which are cultured under conditions in which the promoter induces transient expression of the GFP fusion protein of the present invention, which provides a transient fluorescent label.

BRIEF DESCRIPTION OF THE DRAWINGS

FIG. 6 is a schematic map of the PEST sequence of the fusion EGFP-MODC$_{422-461}$ indicating the position of the mutations.

FIG. 7 is a table summarizing the results obtained measuring persistence of fluorescent signal in transfected CHO K1 Tet-off cells expressing EGFP, EGFP-MODC$_{422-461}$, and the PEST mutants. Transfection was performed in CHO/tTA cells using the procedure given in Example 2. After 24 hours, cells were treated with cycloheximide for 0, 2, and 4 hours, and analyzed for fluorescence by FACS Caliber.

DETAILED DESCRIPTION OF THE INVENTION

Figure 1:
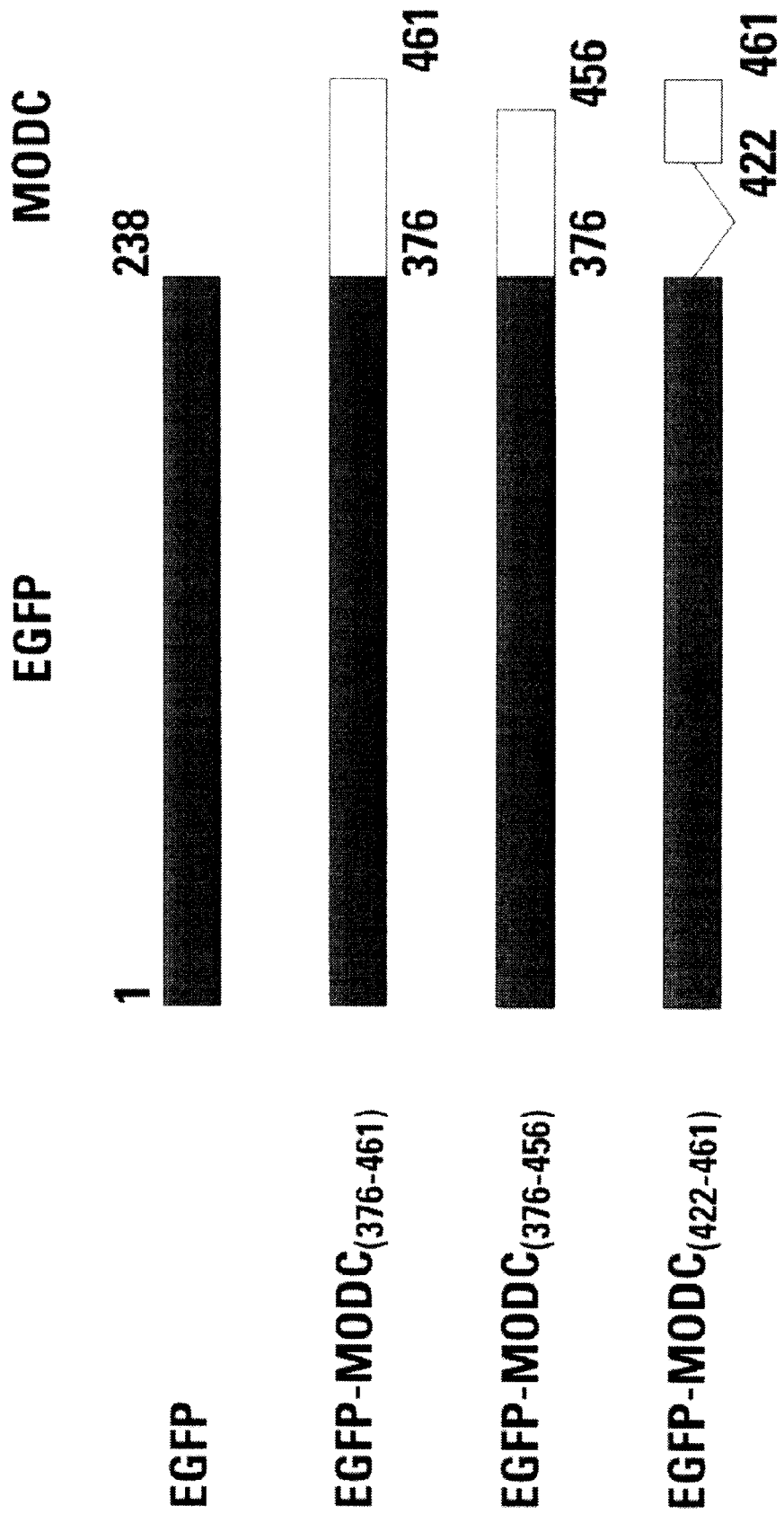
FIG. 1 is a schematic map of EGFP and EGFP-MODC fusion proteins. EGFP is fused with a region of the C terminus of MODC, including amino acids from 376 to 461, 376 to 456 or 422 to 461. The fusion proteins were expressed in CHO K1 Tet-off cells and their fluorescence intensities were compared under a fluorescence microscope.

The invention describes a genetically-engineered fluorescent protein that is destabilized, having a rapid turnover in a cell. More specifically, this fusion protein comprises a fluorescent protein which has a half life of no more than about ten hours and most preferably with a half life of no more than 2 hours. Preferably, the fluorescent protein is selected from the group consisting of EGFP, ECFP and EYFP. In one embodiment, the engineered GFP is a fusion protein of EGFP and a peptide the inclusion of which produces a destabilized protein. An example of such a peptide is the C-terminal region of murine ornithine decarboxylase (MODC). In a specific, illustrative case, the degradation domain of murine ornithine decarboxylase from amino acids 422 to 461 was appended to the C-terminal end of an enhanced variant of GFP (EGFP). The fluorescence intensity of the EGFP-MODC$_{422-461}$ fusion protein in transfected cells was similar to that of EGFP, but the fusion protein, unlike EGFP, dissipated over time in cells treated with cycloheximide. The half-life of the fluorescence of the EGFP-MODC$_{422-461}$ fusion protein was about 2 hours, while that of EGFP was more than 24 hours. The ornithine decarboxylase degradation domain dramatically decreases EGFP stability.

The rapid turnover version of EGFP has at least four advantages over EGFP. The rapid turnover of the EGFP-MODC fusion causes less toxicity to cells expressing the fusion protein. Thus, one advantage is the feasibility of establishing stable cell lines using DNA coding for EGFP-murine ornithine decarboxylase. Further, the destabilized EGFP-MODC decreases EGFP accumulation. Accumulation of fluorescent protein can interfere with the sensitivity of analysis. Thus, the destabilized, rapid turnover fusion protein renders more sensitive results. Additionally, destabilized EGFP can be used as a transient reporter to study transcriptional regulation and/or action of cis-acting regulatory elements. Finally, the EGFP-MODC fusion protein can be used to study processes involving multiple gene expression.

Moreover, the EGFP-MODC fusion protein has the advantages inherent to use of EGFP. For example, the use of EGFP in drug screening assays is particularly advantageous because GFP fluorescence can be detected intracellularly without performing additional expensive steps; e.g. lysing cells, adding exogenous substrates or cofactors, fixing the cell preparation, etc. A single illustration of such an assay is screening test compounds for interruption of the TNF activation pathway, a pathway which ultimately affects apoptosis. Compounds identified in the assay would be useful in controlling the cellular processes involved in cancer and inflammation.

Further, the reporter gene of the present invention can be linked with different enhancer elements and used to monitor diverse biological processes such as heat response, response to heavy metals, glucocorticoid activation or response to cAMP. In particular, destabilized EGFP is useful for studying developmental processes where genes are transiently expressed, dynamics of protein transport, localization of proteins within cells, and periodic and cyclical expression of genes that control unique biological phenomena such as circadian rhythms. Indeed, other applications of the EGFP-MODC fusion protein in screening assays would be appreciated readily by those having ordinary skill in this art.

Moreover, by using an inducible promoter, expression of the EGFP-MODC fusion protein is activated or deactivated at will, making a construct expressing the protein useful in cell lineage studies. Prior art GFP models express GFP at levels that are toxic and interfere with cell development, thus making cell lineage studies impossible. Additionally, destabilized EGFP can be used as a reporter to study the kinetics of mRNA transcription from a regulated promoter, because the fluorescence intensity of destabilized EGFP is a direct measure of the level of gene expression at any given time point.

As used herein, the term "GFP" refers to the basic green fluorescent protein from *Aequorea Victoria*, including prior art versions of GFP engineered to provide greater fluorescence o r fluoresce in different colors. The sequence of *A. Victoria* GFP has been disclosed in Prasher D.C. et al. (1992) *Gene* 111:229–33.

As used herein, the term "EGFP" refers to GFP which has been "humanized", as reported in Kain et al. (1995) *Bio-*

*techniques* 19(4):650–55. "Humanized" refers to changes made to the GFP nucleic acid sequence to optimize the codons for expression of the protein in human cells.

As used herein, the term "peptide which produces a destabilized protein" refers to a sequence of amino acids or a peptide which promotes destabilization or rapid turnover of the protein of which it is a part; i.e., by inducing protein degradation. The PEST sequence described herein is one such sequence. Other sequences known in the art are those peptides that promote phosphorylation and protein-protein interactions.

As used herein, the term "EGFP-MODC" refers to EGFP fused at its C terminus to murine ornithine decarboxylase sequences.

As used herein, the term "P438A" refers to an EGFP-MODC fusion protein in which the proline at position 438 in the murine ornithine decarboxylase sequence (a proline residing in the PEST portion of the sequence) has been replaced with alanine. The same nomenclature is used for EGFP-MODC mutants P426A/P427A; E428A/E430A/E431A; E444A; S440A; S445A; T436A; D433A/D434A; and D448A. Further elucidation is shown in FIG. 6.

As used herein, the term "half life" refers to the period of time in which half of the fluorescent signal from a fluorescent protein expressed in cells disappears and half remains.

As used herein, the term "Tc" refers to tetracycline.

As used herein, the term "CHX" refers to cycloheximide.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D.N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984).

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

Transcriptional and translational control sequences are DNA regulatory sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is a n identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "reporter gene" refers to a coding sequence attached to heterologous promoter or enhancer elements and whose product may be assayed easily and quantifiably when the construct is introduced into tissues or cells.

Transcriptional and translational control sequences are DNA regulatory sequences, such as promoters, enhancers, polyadenylation signals, terminators, and the like, which provide for the expression of a coding sequence in a host cell.

The amino acids described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552–59 (1969), abbreviations for amino acid residues are shown in the following Table of Correspondence:

| Y | Tyr | tyrosine |
|---|-----|----------|
| G | Gly | glycine |
| F | Phe | Phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of aminoterminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

Thus, the present invention is directed to a fusion protein comprising GFP so that the resulting fusion protein has a half life of no more than about ten hours and as little as less than one hour. In a preferred form, the GFP is EGFP. Preferably, the fusion protein comprises EGFP fused to a PEST sequence-containing portion of a C-terminus of murine ornithine decarboxylase (MODC). Representative examples of PEST sequence-containing portion of a C-terminus of murine ornithine decarboxylase include $MODC_{376-461}$, $MODC_{376-456}$, $MODC_{422-461}$, P426A/P427A, P438A, E428A/E430A/E431A, E444A, S440A, S445A, T436A, D433A/D434A and D448A. One example of the GFP fusion protein of the present invention has the sequence shown in SEQ ID No. 1.

The present invention is also directed to an isolated DNA molecule encoding the fusion protein which comprises a fluorescent protein selected from the group consisting of EGFP, ECFP and EYFP. One example of the isolated DNA of the present invention has the sequence shown in SEQ ID No: 2. The present invention is also directed to a vector capable of expressing this isolated DNA molecule. In one form, the vector contains a inducible promoter and is a tetracycline-regulated expression vector.

The present invention is also directed to a method of producing a stable cell line that expresses a fluorescent protein, e.g., GFP, comprising the step of transfecting cells with a vector disclosed herein.

In addition, the present invention is directed to a method of assaying activation or deactivation of promoters or other transcriptional or translational elements with a transient fluorescent reporter protein, comprising the steps of transfecting cells with an expression vector comprising a fusion protein having a half life of no more than about ten hours, preferably less than four hours and most preferably less than one hour, wherein the fusion protein is under the influence of the promoter, transcriptional or translational element, and detecting the presence, absence or amount of fluorescence in said cells. In this method, the amount of fluorescence present in the cell is a measure of the fluorescent protein that is being expressed. Detecting differences in fluorescence intensity between cells expressing the fluorescent protein under different transcriptional or translational elements of interest is a rapid and straightforward procedure to measure effects of these transcriptional or translational elements. Further, an additional step may be performed wherein transfected cells are treated with a compound of interest to determine the effect of the compound of interest on the transcriptional or translational elements. Detecting a change in fluorescence upon treatment of the cells with the compound of interest is a rapid and straightforward procedure to measure the effects of the compounds on interest on the transcription or translation of the expressed fusion protein.

In addition, the present invention is directed to methods of studying cell lineage comprising the steps of transfecting undifferentiated cells with a vector capable of expressing the destabilized fluorescent fusion protein of the present invention, growing the undifferentiated cells under conditions in which the undifferentiated cells become differentiated cells, and detecting an absence or presence of fluorescence in the differentiated cells. Further, the present invention provides a method of using a fusion protein described herein in cell localization studies, comprising the steps of transfecting cells with an expression vector comprising a fluorescent fusion protein having a half life of no more than ten hours and preferably less than four hours wherein the fusion protein is linked to a putative cell localization element, growing the cell and detecting a location of fluorescence in the cells.

EXAMPLE 1

Construction of DNA Expression Vectors

The cDNAs encoding EGFP and the C terminus of murine ODC (MODC) were amplified with pfu DNA polymerase (Stratagene, Inc., La Jolla, Calif.). EGFP was amplified with a pair of primers: 5' incorporated with a SacII recognition sequence and 3' with a Hind III sequence. The stop codon of EGFP was deleted from its C-terminus in order to make an open reading frame with the C terminus of murine ODC. The C terminus of murine ODC was also amplified with a pair of primers: 5' incorporated with a Hind III recognition sequence and 3' with an EcoRI sequence. Two amplified PCR products were ligated at the Hind III site and the fusion was cloned into pTRE expression vector, Tc-regulated expression system (Gossen M., and Bujard H. (1992) *Proc. Natl. Acad. Sci.* 89: 5547–5551).

Using these methods, fusion proteins of EGFP-MODC were constructed. The EGFP-$MODC_{376-461}$ fusion protein included the complete C-terminus of murine ornithine decarboxylase. EGFP-$MODC_{376-456}$ and EGFP-$MODC_{422-461}$ included only portions of the murine ornithine decarboxylase degradation domain, though both included the PEST sequence. Further, key amino acids of the PEST sequence in the fusion protein were then mutated to alanine using a homology extension procedure (Rogers, et al., (1986) *Science* 234, 364–368). The PEST mutants included P426A/P427A; P438A; E428A/E430A/E431A; E444A; S440A; S445A; T436A; D433A/D434A; and D448A.

EXAMPLE 2
Cell Transfection

The construct DNAs were purified and transfected into CHO K1-off cells for determination of protein degradation. CHO K1-off cells are CHO cells which were pre-transfected by a fusion protein of the tet-repressor and the herpes simplex virus VP16 gene (tTA). This pre-transfection allows expression of the gene coding for the fusion protein on a pTRE vector (Gossen and Bujard, ibid), which in turn initiates transcription by binding, to a modified CMV promoter with tet-repressor binding elements. This binding can be blocked by tetracycline; hence, the expression can be controlled by tetracycline. The DNAs were introduced into these cells by CLONfectin (CLONTECH Laboratories, Inc., Palo Alto). After 24 hours, transfected cells were subject to functional analyses.

EXAMPLE 3
Fluorescence Analysis

Cells were cultured on top of cover-slips to allow observation under a fluorescence microscope. After transfection, the cells were incubated at 37° C. for 24 hours on the cover-slips and then fixed with 4% paraformaldehyde for 30 minutes. The cover-slips were mounted on a glass slide for fluorescence examination with a Zeiss Axioskop Model 50 fluorescent microscope. To determine protein turnover, the cells were treated with cycloheximide at a final concentration of 100 µg/ml for variable times before paraformaldehyde fixation.

For FACS analysis, the transfected cells as well as cycloheximide-treated cells were collected by EDTA treatment and the cell pellets were resuspended in 0.5 ml of PBS. The cell suspensions were then analyzed for fluorescence intensity by FACS Calibur (Becton Dickson, Inc., San Jose, Calif.). EGFP was excited at 488 nm, and emission was detected using a 510/20 bandpass filter.

EXAMPLE 4
Western Blot Analysis

For western blot analysis, transfected control cells as well as cycloheximide-treated cells were collected in PBS and sonicated to prepare cell lysates. Proteins were separated by SDS-PAGE. EGFP and MODC fusion proteins were detected by a monoclonal antibody against GFP after the proteins were transferred onto a membrane. The detection was visualized with a chemiluminescent detection kit (CLONTECH).

EXAMPLE 5
Determination of EGFP-MODC Protein Stability

The C terminus of murine ornithine decarboxylase, from amino acids 376 to 461, has been shown to induce TbODC degradation in mammalian cells. To demonstrate that the degradation domain could also induce EGFP degradation, murine CDC sequence was appended to the C-terminal end of EGFP to make a first fusion EGFP-MODC construct (FIG. 1). The EGFP-MODC$_{376-461}$ fusion construct was expressed with the Tc-regulated expression vector (pTRE). Fluorescence intensity of the EGFP-MODC$_{376-461}$ fusion protein was examined under a fluorescence microscope after being transiently expressed in CHO K1-off cells. The fluorescence intensity of the EGFP-MODC$_{376-461}$ fusion protein was very low (FIG. 1). Although it was believed that the lower fluorescence of the protein was due to rapid degradation, an EGFP fusion protein with such a low signal intensity would not be useful for most research applications.

If the rapid degradation indeed accounted for the lower fluorescence of the EGFP-MODC$_{376-461}$, the fluorescence intensity the fusion protein could be increased by decreasing the rate of its degradation. The size of the C-terminal extension of murine ornithine decarboxylase can determine the rate of degradation. Deletion from either end of the degradation domain has yielded truncated proteins with a decreased rate of degradation, and removal of the last five amino acids from murine ornithine decarboxylase dramatically decreases degradation of murine ornithine decarboxylase (Ghoda, L., et al. (1992) Mol. Cell. Biol. 12, 2178–2185). A TbODC fusion with a smaller extension starting at amino acid 422 has degraded more slowly than the longer extension starting at amino acid 376 (Li, X., and Coffino, P. (1993) Mol. Cell. Biol. 13: 2377–2383). Therefore, two smaller extensions, one from amino acid 422 to 456 and the other from 422 to 461, also were appended to the C-terminus of EGFP to make EGFP-MODC$_{376-456}$ and EGFP-MODC$_{422-461}$ (FIG. 1). Both of these fusion proteins contain the PEST sequence. After transfection, the fluorescence intensities of both fusion proteins were examined with fluorescence microscopy. Results indicated that both had a higher relative fluorescence intensity than EGFP-MODC$_{376-461}$, particularly the fusion protein EGFP-MODC$_{422-461}$. As can be seen in FIG. 1, the fluorescence of this latter fusion protein is similar to EGFP.

Figure 2:
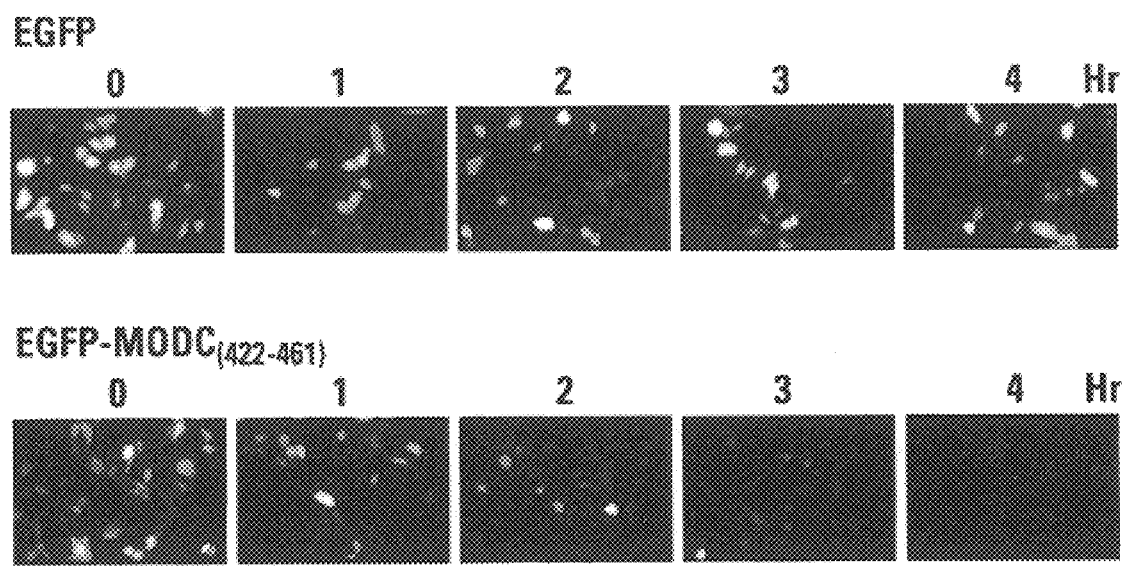
FIG. 2 shows the fluorescence stabilities of EGFP and EGFP-MODC$_{422-461}$ in cells in the presence of cycloheximide and examined with a fluorescence microscope. CHO K1 Tet-off cells were transfected with vectors expressing these two proteins. After 24 hours, the transfected cells were treated with 100 mg/ml cycloheximide for 0, 1, 2, 3, and 4 hours.

EXAMPLE 6
Further Characterization of EGFP-MODC$_{422-461}$ Protein Stability Next, it was determined whether the C terminal extension from amino acids 422 to 461 was able to induce EGFP degradation in vivo. To do this, the construct first was transiently transfected into CHO K1-off cells, and the half life of the fusion protein was determined by blocking protein synthesis with cycloheximide (CTX). At 24 hours post-transfection, the cells were treated with 100 µg/ml cycloheximide for 0, 1, 2, 3, and 4 hours. The change in fluorescence intensity of the transfected cells was examined by fluorescence microscopy, and the results are shown in FIG. 2. The fluorescence intensity of the fusion protein in the cells gradually decreased as cycloheximide treatment was extended, indicating that the EGFP-MODC$_{422-461}$ fusion protein is unstable. After 4 hours of treatment with cycloheximide, less than half of the fluorescent intensity existed compared to the intensity of the fluorescence of the cells time zero. These results indicated that the half life of the fusion protein is less than 4 hours.

The EGFP-MODC$_{422-461}$ was then compared to EGFP in the same assay. There was no significant change in the fluorescence intensity of EGFP in the EGFP-transfected cells four hours after protein synthesis stopped (FIG. 2), indicating the half life of EGFP is longer than 4 hours. This is consistent with other reports on GFP. This result supports the conclusion that EGFP is a stable protein when expressed in mammalian cells and that the protein product of the EGFP-MODC$_{422-461}$ construct is unstable.

Figure 3:
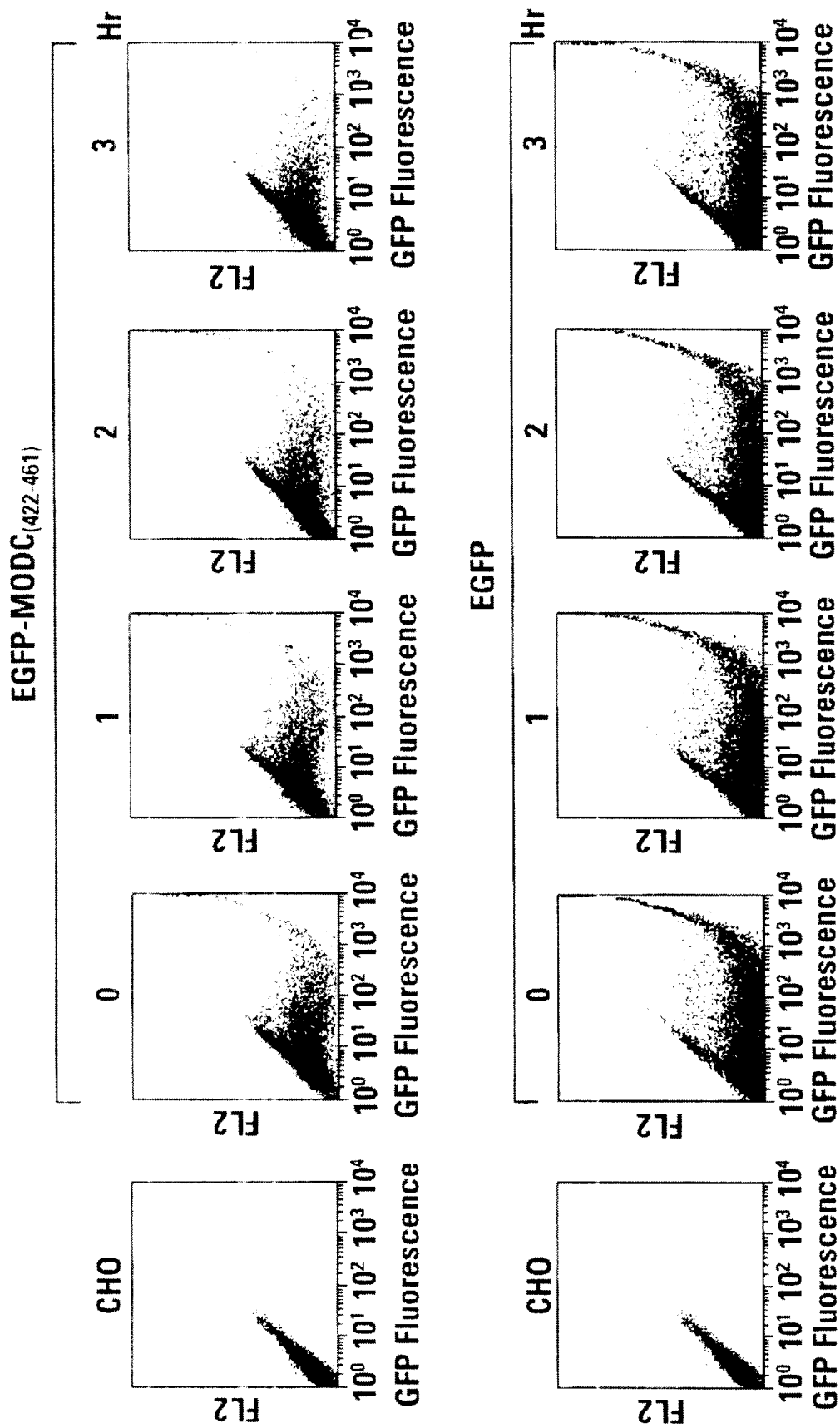
FIG. 3 shows flow cytometric analysis of the fluorescence stabilities of EGFP and EGFP-MODC$_{422-461}$. CHO K1 Tet-off cells were transfected with EGFP and EGFP-MODC$_{422-461}$. After 24 hours, the transfected cells were treated with 100 µg/ml cycloheximide for 0, 1, 2, and 3 hours. The treated cells were collected with EDTA and 10,000 cells were subjected to FACS analysis
Figure 3:
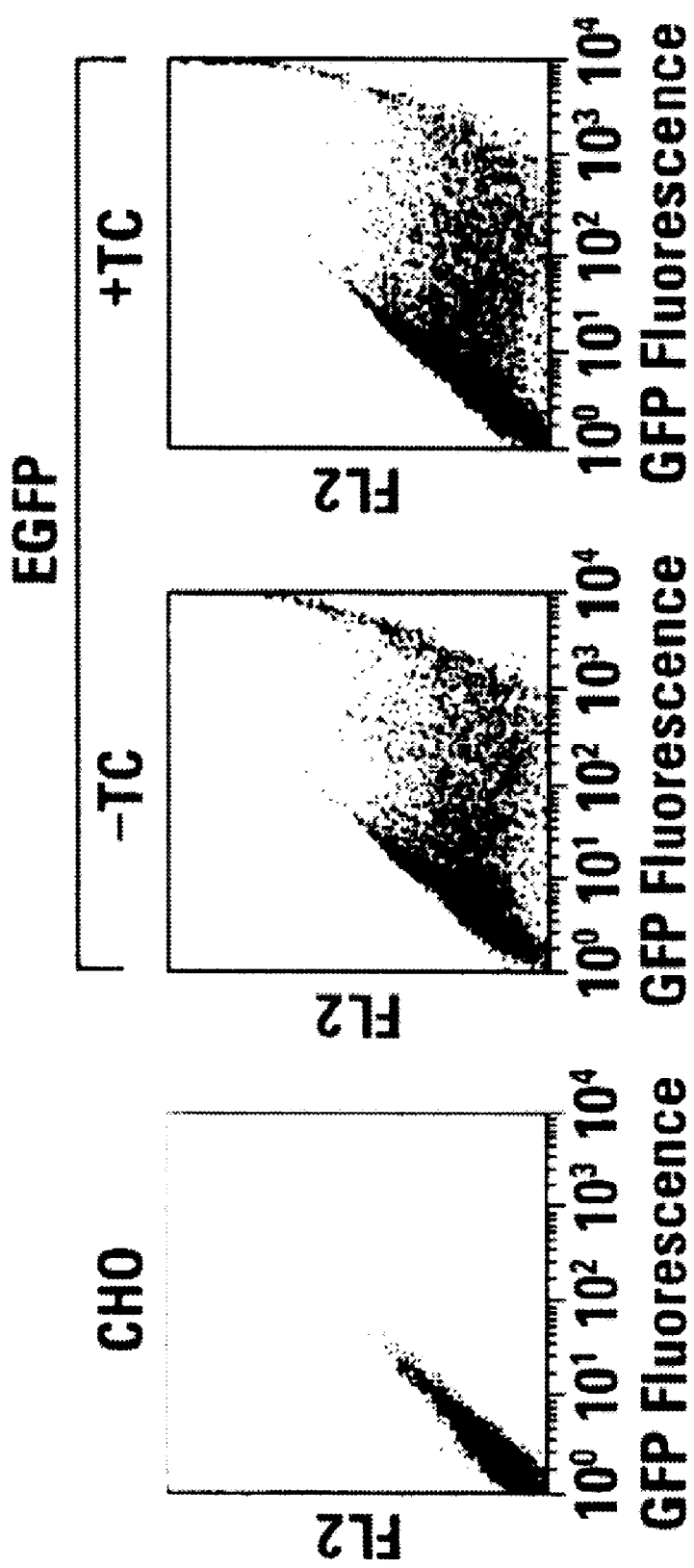

In order to determine more accurately the half lives of the EGFP-MODC fusion protein and EGFP, the change in fluorescence of these two proteins was quantified by flow cytometry. Transfected cells, after treatment with cycloheximide for 0, 1, 2 and 3 hours, were collected with EDTA, and 10,000 cells were subjected to FACS analysis. The results agreed with the fluorescence microscope observations; i.e., the fluorescence of the fusion protein gradually decreased as cycloheximide treatment was extended (FIG. 3).

Figure 4:
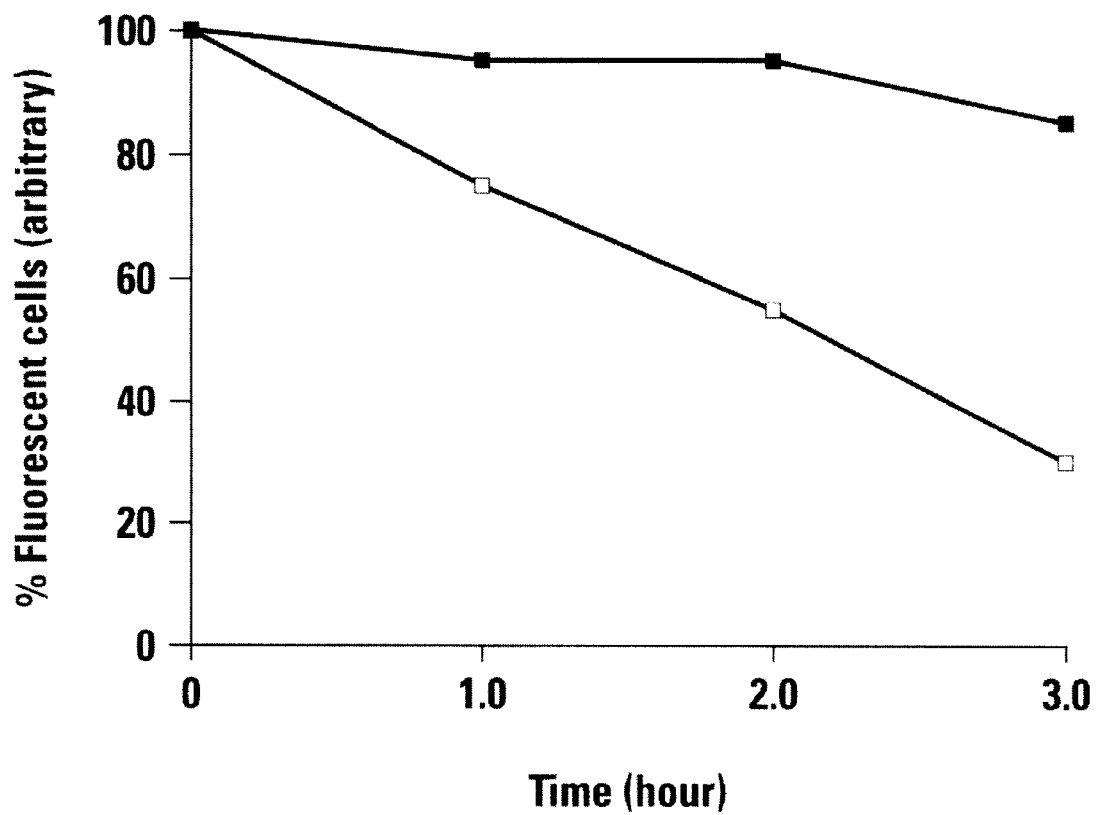
FIG. 4 is a graph summarizing the flow cytometric data from FIG. 3, demonstrating that EGFP-MODC$_{422-461}$-transfected cells rapidly lose fluorescence after cycloheximide treatment, whereas EGFP cells maintain fluorescence.

The graph in FIG. 4 summarizes the FACS data and shows that approximately 50% of untreated cells maintained fluorescence after 2 hours of cycloheximide treatment, indicating that the half life of the fusion protein is about 2 hours. EGFP-transfected cells were subjected to similar analysis, and results showed that the EGFP fluorescence did not change significantly during treatment with cycloheximide. Indeed, after 4 hours of cycloheximide treatment, EGFP cells still had more than 80% of fluorescence relative to untreated EGFP cells. In short, the half life of the EGFP fusion is suitably reduced and the half life of EGFP is significantly more than 4 hours.

Cycloheximide treatment cannot be prolonged for greater than 4 hours since it is toxic to cells, causing apoptosis. However, because the inducible expression system used in these studies is regulated by tetracycline (Gossen M., and Bujard H. (1992) *Proc. Natl. Acad. Sci.* 89: 5547–5551), EGFP synthesis can be stopped simply by adding tetracycline. To determine more precisely the half life of EGFP, the fluorescence intensities of EGFP transfected cells after 24 hours, in both the presence and absence of tetracycline, was monitored. EGFP first was allowed to be expressed for 24 hours after transfection. The transfected cells then were cultured in the presence or absence of tetracycline for another 24 hours and collected for analysis by flow cytometry. No difference in fluorescent intensity was detected between these two types of cells (-TC and +TC in the bottom panel of FIG. 3), indicating that fluorescence did not change in the 24 hours after EGFP protein synthesis shut-off. These results indicate that the half life of EGFP is more than 24 hours.

Figure 5:
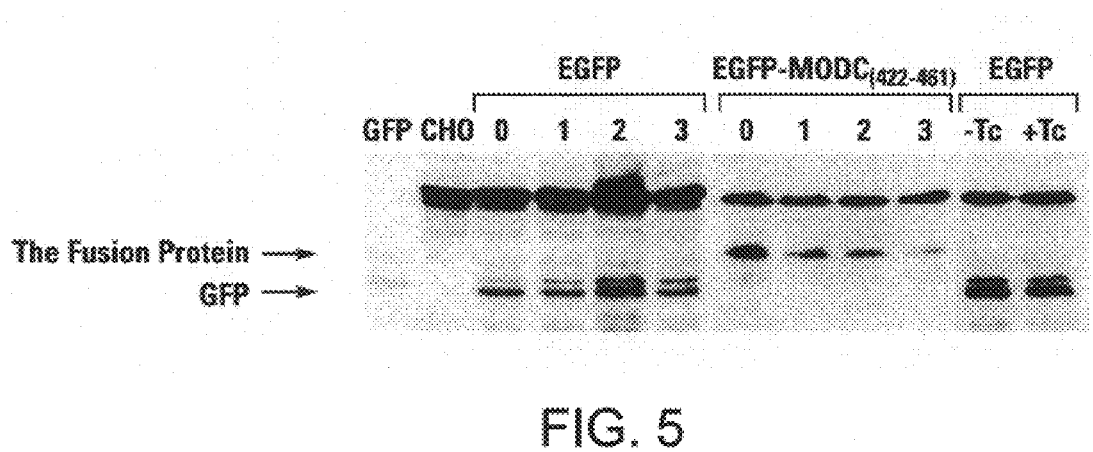
FIG. 5 is a photograph of western blot analysis of protein stabilities of EGFP and EGFP-MODC$_{422-461}$. Cells collected during flow cytometry were used for preparing cell lysates. The cell lysates were subject to SDS gel electrophoresis and transferred onto a membrane. EGFP and the EGFP fusion protein were detected with a monoclonal antibody against GFP.

To examine if the half life of the EGFP and the EGFP fusion protein of the present invention correlated with the amount of fluorescence, degradation of the fusion protein was monitored by western blot analysis. Both the EGFP and EGFP-MODC$_{422-461}$ transfected cells that were used for flow cytometry in FIG. 3 were also used for Western blot analysis with a monoclonal antibody against GFP. As shown in FIG. 5, no detectable change in the level of EGFP protein was found among cells treated for 0–3 hours with cycloheximide, indicating that EGFP is stable during 3 hour cycloheximide treatment.

EGFP fusion proteins with the MODC modification of the present invention were also detected by a GFP monoclonal antibody. The size of the fusion protein was about 31 kDa. Unlike EGFP, however, the EGFP fusion protein was unstable. The level of the fusion protein fell dramatically by the end of the 3-hour cycloheximide treatment; in fact, less than one half of the control EFGP fusion protein was left at one hour, indicating that the half life of the fusion protein may be one hour or less. The difference in the measured half life using flow cytometry versus western blot analysis likely is due to the fact that both premature (i.e. non-fluorescent) and mature GFP are detected by western analysis. However, the formation of EGFP chromophore is post-translational and proceeds with a half-time of about 25 minutes (Cormack, et al., (1996) *Gene* 173, 33–38). GFP in the context of this invention is important at its fluorescence level as a reporter, rather than at a protein level—the half life of EGFP fluorescence is more important. The fluorescence half life of EGFP-MODC$_{422-461}$ in vivo is approximately 2 hours.

The amino acid sequence of the EGFP-MODC$_{422-461}$ protein is as follows:
MVSKGEELFTGVVPILVELDGDVNGH-
KFSVSGEGEGDATYGKLTLKFICTTGK LPVP-
WPTLVTTLTYGVQCFSRYPDHMKQHD-
FFKSAMPEGYVQERTIFFKDDG
NYKTRAEVKFEGDTLVNRIELKGID-
FKEDGNILGHKLEYNYNSHNVYIMADKQ
KNGIKVNFKIRHNIEDGS-
VQLADHYQQNTPIGDGPVLLPDNHYLSTQSALSKD
PNEKRDHMVLLEFVTAAGITLGMDE-
LYKKLSHGFPPEVEEQDDGTLPMSCAQ ESGM-
DRHPAACASARINV (SEQ ID No:1); and the DNA sequence which encodes the EGFP-MODC$_{422-461}$ protein is as follows:

```
atgg          tgagcaaggg  cgaggagctg  ttcaccgggg  tggtgcccat  cctggtcgag ctggacggcg    acgtaaacgg  ccacaagttc  agcgtgtccg  gcgagggcga  gggcgatgcc acctacggca    agctgaccct  gaagttcatc  tgcaccaccg  gcaagctgcc  cgtgccctgg cccaccctcg    tgaccaccct  gacctacggc  gtgcagtgct  tcagccgcta  ccccgaccac atgaagcagc    acgacttctt  caagtccgcc  atgcccgaag  gctacgtcca  ggagcgcacc atcttcttca    aggacgacgg  caactacaag  acccgcgccg  aggtgaagtt  cgagggcgac accctggtga    accgcatcga  gctgaagggc  atcgacttca  aggaggacgg  caacatcctg gggcacaagc    tggagtacaa  ctacaacagc  cacaacgtct  atatcatggc  cgacaagcag aagaacggca    tcaaggtgaa  cttcaagatc  cgccacaaca  tcgaggacgg  cagcgtgcag ctcgccgacc    actaccagca  gaacacccc   atcggcgacg  gccccgtgct  gctgcccgac aaccactacc    tgagcaccca  gtccgccctg  agcaaagacc  ccaacgagaa  gcgcgatcac atggtcctgc    tggagttcgt  gaccgccgcc  gggatcactc  tcggcatgga  cgagctgtac  aagaagctt-agccatg gcttcccgcc  ggaggtggag  gagcaggatg  atggcacgct  gcccatgtct tgtgcccagg    agagcgggat  ggaccgtcac  cctgcagcct  gtgcttctgc  taggatcaat gtgtagatgc (SEQ ID No:2).
```

EXAMPLE 7
Analysis of the PEST Sequence

The C terminus of mouse ornithine decarboxylase contains a PEST sequence from amino acids 423 to 449. There are three proline residues, four glutamic acid residues, two serine residues, and one threonine residue (FIG. 6). To evaluate the contribution of each amino acid in the PEST motif to the rate of protein degradation, each Pro, Glu, Ser, and Thr residue in the PEST region of EGFP-MODC fusion protein was mutated to Ala. Degradation was monitored by the change of fluorescence. Each construct was transiently transfected into CHO K1-off cells. After treatment in the presence of cycloheximide for 0, 2, and 4 hours, the cells were collected for flow cytometry analysis. Data are shown in FIG. 7.

Mutation of the proline residue at amino acid 438 stabilized the protein. After 4 hours of cycloheximide treatment, the percentage of fluorescent cells was still greater than 60%. Thus, the half life of the P438A mutant is more than double that of EGFP-MODC$_{422-461}$ suggesting that the existence of proline at 438 contributes to the instability of the fusion protein. Mutation of the prolines at amino acid positions 426 and 427 did not extend the half life. Instead, the half life of P426A/P427A is even shorter than that of EGFP-MODC$_{422-461}$, indicating that these proline residues may stabilize the protein. Similar results were obtained with mutations to the glutamine and serine in the fusion construct. The half lives of mutant E444A and S440A are longer than that of that EGFP-MODC$_{422-461}$, but E428A/E430A/E431A and S445A became more unstable, with only 20% or 29% of the cells retaining fluorescence after two hours of treatment.

The PEST sequence is often flanked by basic amino acids (Rogers, et al., (1986) *Science* 234, 364–368). To show the involvement of these flanking amino acid residues in protein instability, histidine 423, arginine 449 and histidine 450 were mutated to alanine. Substitutions of alanine for the arginine and histidine at positions 449 and 450 dramatically increased protein stability, suggesting that these two amino acids are required for efficient protein degradation. Mutation of the His at amino acid 423 did not change protein stability.

The amino acid sequence of the C-terminus of murine ornithine decarboxylase, MODC$_{422-461}$, is as follows: MGFPPEVEEQDDGTLPMSCAQESGMDRH (SEQ ID NO: 3). The amino acid sequences of the PEST mutants P426A/P427A (SEQ ID NO: 4), P438A (SEQ ID NO: 5), E428A/E430A/E431A (SEQ ID NO: 6), E444A (SEQ ID NO: 7), S440A (SEQ ID NO: 8), S445A (SEQ ID NO: 9), T436A (SEQ ID NO: 10), D433A/D434A (SEQ ID NO: 11), D448A (SEQ ID NO: 12), H423A (SEQ ID NO: 13), and R449A/H450A (SEQ ID NO: 14) are shown in FIG. 6.

EXAMPLE 8
Cell Line Expressing dEGFP With Tet Expression System

CHO K1-tet off cells were transfected with pTRE-EGFPMODC$_{422-461}$ and pTK-hygromycin. The transfection was performed with a CLONfectin kit (CLONTECH). The transfected cells were selected in the presence of 200 µg/ml hygromycin and resistant colonies were screened for fluorescence under a fluorescent microscope. The individual single colonies of the fluorescent cells were transferred to new plates. As in the transiently transfected cells, destabilized EGFP in the stably-transfected cells was regulated by tetracycline, and degradation was detectable by adding cycloheximide to block protein synthesis. The resulting stably-transfected cell line can be used for many analyses, including drug screening; in particular, it can be used to screen for drugs that block either the transcriptional induction of destabilized EGFP during the transition from the presence of tetracycline to the absence of tetracycline, or for drugs that inhibit protein degradation after the addition of cycloheximide.

EXAMPLE 9
Destabilized ECFP and EYFP

CFP (cyan) and YFP (yellow) are color variants of GFP. CFP and YFP contain 6 and 4 mutations, respectively. They are Tyr66Try, Phe66Leu, Ser65Thr, Asn145Ile, Met153Thr, and Val163Ala in CFP and Ser65Gly, Val168Leu, Ser72Ala, and Thr203Tyr. The enhanced CFP (ECFP) and YFP (EYFP) are encoded by genes with human-optimized codons. ECFP is excited at 433 nm and emits at 475 nm. EYFP is excited at 523 or 488 nm and emits at 527 nm.

Figure 8:
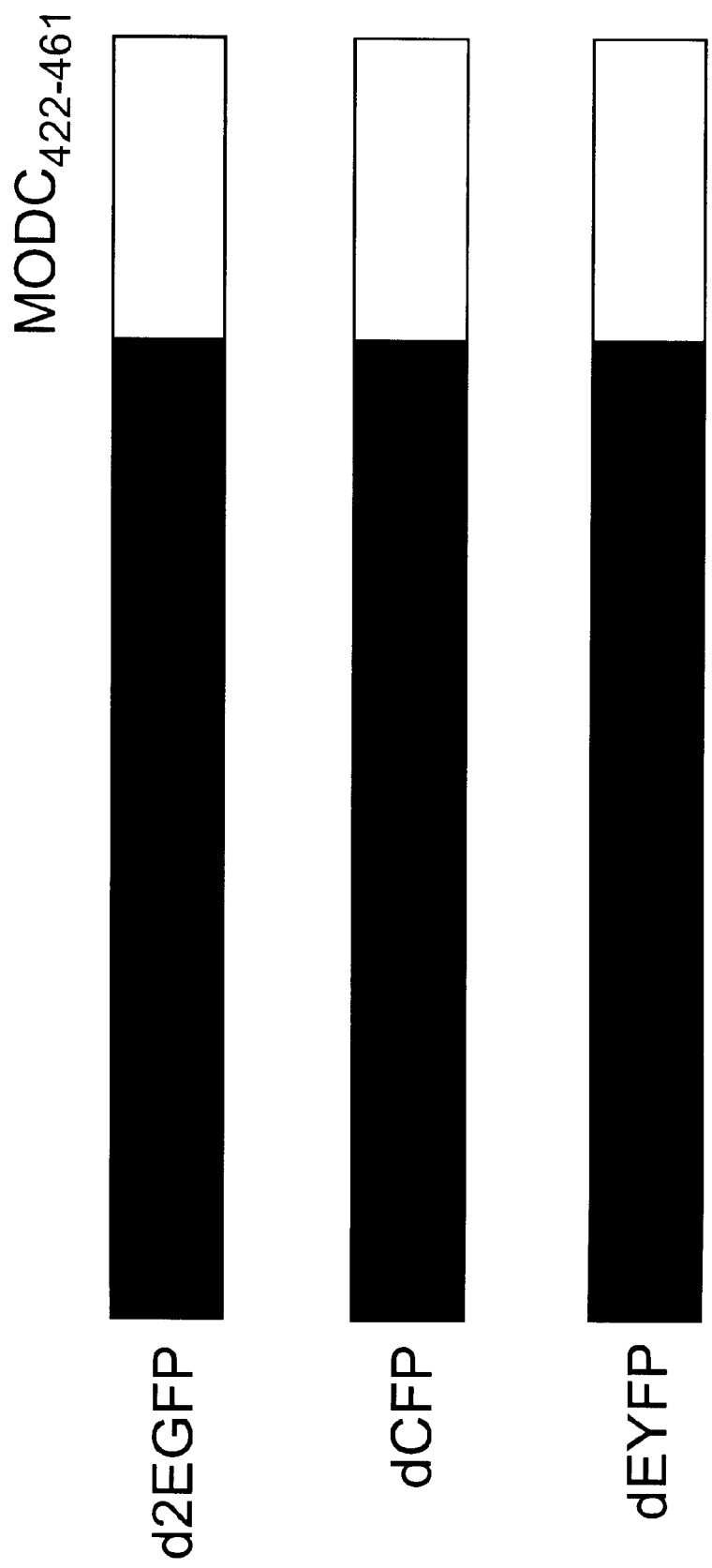
FIG. 8 shows a schematic illustration of d2EGFP, dECFP and dEYFP.

Using the same strategy described above to create dEGFP, dECFP and dEYFP were generated by appending the C terminus of mouse ornithine decarboxylase to the C terminus of each of these two proteins (FIG. 8). The half-lives of dECFP and dEYFP were determined by transfecting pTRE-dECFP and pTRE-dEYFP into CHO/tTA cells, stopping protein synthesis by adding CHX, and subjecting to fluorescence microscopy. Both proteins were unstable in the presence of CHX. Two hours after treatment with CHX, half of fluorescence of these two proteins disappear indicating substantially reduced half lives for these proteins as compared to wild type.

These two color variants of destabilized proteins can be used together for two-color detection. For example, the dECFP gene can be linked to the NFkB binding sequence and the dEYFP to the NFAT binding sequence. Introduction of these two reporter fusions to a single cell allows detection simultaneous of two transcription factors or two signaling pathways simply by monitoring the relative fluorescence of the two colors.

EXAMPLE 10
Degradation Rate and Induction Fold of dEGFP

Figure 9:
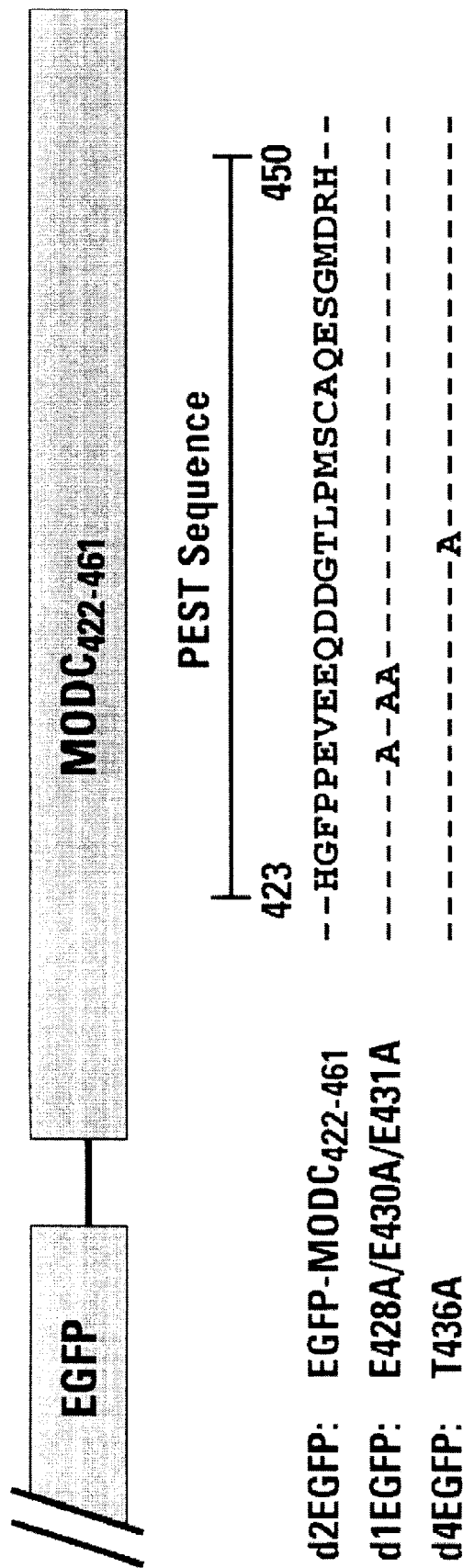
FIG. 9 shows the construction of destabilized EGFP Variants.
Figure 10:
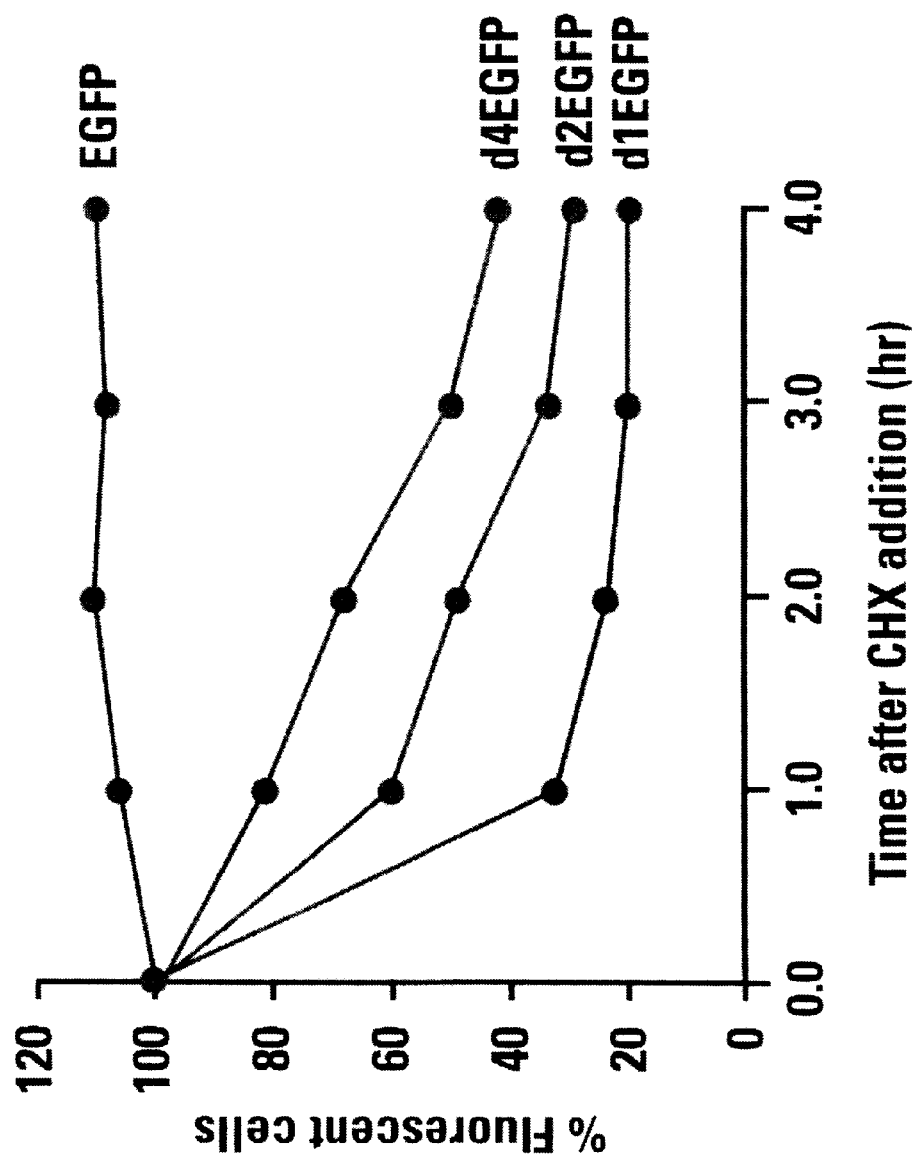
FIG. 10 shows the fluorescence stabilities of EGFP and dEGFP Variants.

By mutating key amino acids of the PEST sequence of dEGFP, a number of mutants with different half lives were created. They were designated d1EGFP and d4EGFP, reflective of their half lives (FIG. 9). The d1EGFP mutant has a half-life of less than 1 hour and the d4EGFP mutant has a half-life of approximately 4 hours (FIG. 10). The EGPP-MODC$_{422-461}$ was designated d2EGFP because its half-life is about 2 hours.

Figure 11:
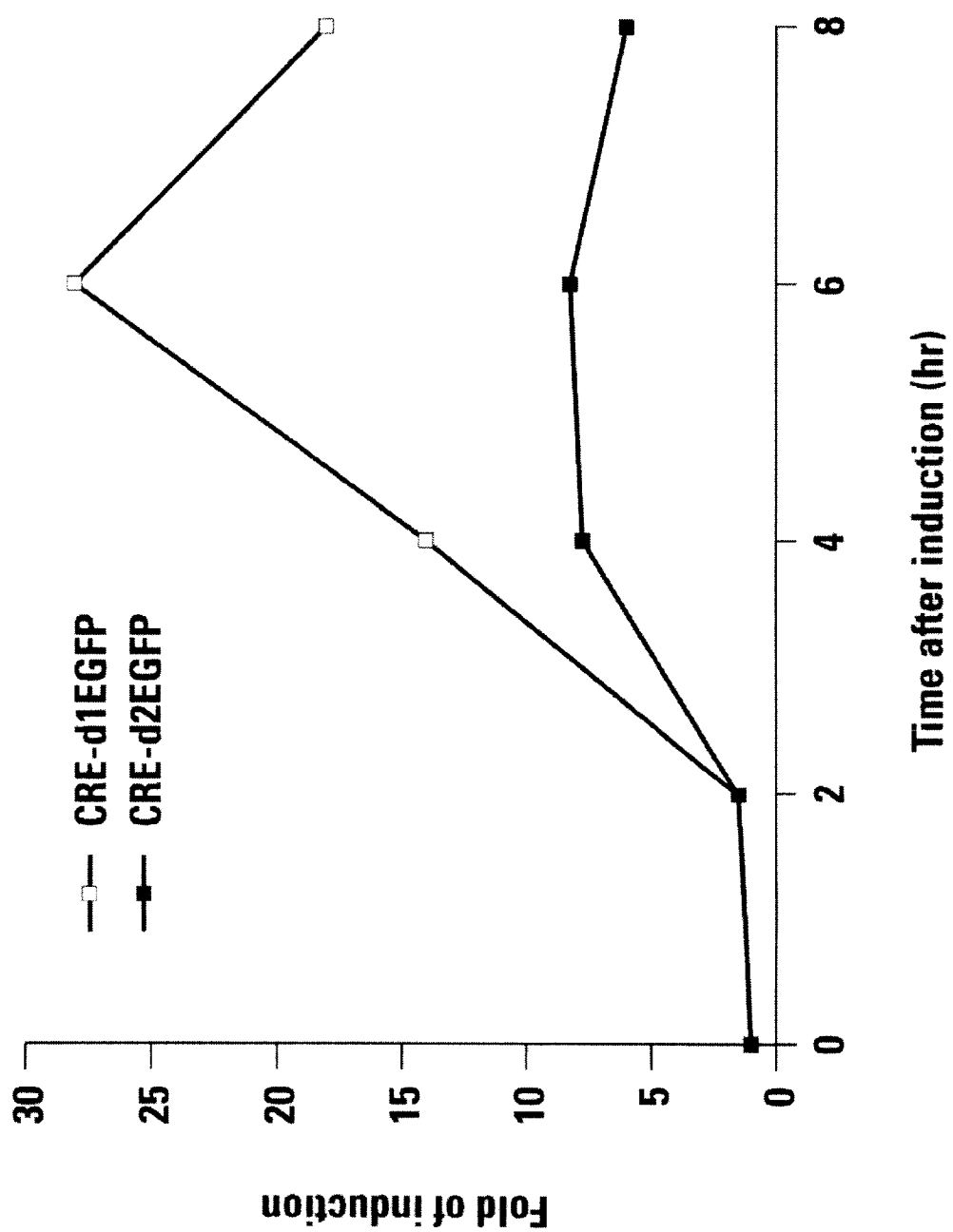
FIG. 11 shows the increase in induction by CRE-d1EGFP and CRE-d2EGFP.

The outstanding character of dEGFP proteins, when compared to EGFP, is that they exhibit a rapid turnover resulting in less accumulation of the destabilized proteins even at basal-level activity. Therefore, d2EGFP is a much more sensitive transcription reporter that EGFP, as has been demonstrated with the system of TNF-mediated NFkB activation. Because d1EGFP has a shorter half-life than d2EGFP, d1EGFP is more sensitive than d2EGFP when used as a transcription reporter. To illustrate this, d1EGFP and d2EGFP genes were linked to cAMP regulated element (CRE) and their responses to forskolin for each fusion construct tested. Four-fold induction was obtained when d2EGFP was used as the reporter, however more than 12-fold induction was achieved when d1EGFP used (FIG. 11). These results indicate that a more rapid turnover of the GFP molecue achieves higher induction and enhanced sensitivity.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of assaying the positive or negative regulatory function of a transcriptional or translational control sequence which controls or regulates the expression of a coding sequence in a host cell with a transient fluorescent reporter protein, comprising the steps of:
   a) transfecting cells with an expression vector comprising a DNA sequence that codes for a fluorescent fusion protein comprising a Green Fluorescent Protein (GFP) and a PEST sequence, wherein said fusion protein has a half life of no more than about ten hours, and wherein said expression vector contains said transcriptional or translational control sequence that may affect the expression of said fluorescent fusion protein;
   b) transfecting cells with a control expression vector comprising a DNA sequence that codes for said fluorescent fusion protein, wherein said control expression vector does not contain said transcriptional or translational control sequence; and
   c) detecting a presence, absence or amount of fluorescence in said cells, wherein an increase or decrease in fluorescence in cells transfected with the vector containing the control sequence compared to cells transfected with the vector not containing the control sequence indicates a positive or negative regulatory function, respectively for said transcriptional or translational control sequence.

2. The method of claim 1, wherein said transcriptional or translational control sequences are selected from the group consisting of a promoter, an enhancer, a transcription terminator, and a polyadenylation signal.

3. The method of claim 1 wherein the GFP is wild type GFP, GFPS65T, humanized GFP, EGFP, blue-emitting GFP, cyan-emitting GFP or yellow-emitting GFP.

4. The method of claim 1 the PEST sequence is selected from the group consisting of a murine ornithine decarboxylase (MODC) PEST sequence, amino acids 376–461 of MODC, amino acids 376–456 of MODC and amino acids 422–461 of MODC.

5. The method of claim 1 wherein the PEST sequence is selected from the group consisting of variants of $MODC_{376-461}$, $MODC_{376-456}$, and $MODC_{422-461}$, containing amino acid substitutions selected from the group consisting of P26A/P427A, P438A, E428A/E430A/E431A, E444A, S440A, S445A, T436A, D433A/D434A and D448A.

6. A method of assaying the positive of negative effect of a test compound on the regulatory function of a transcriptional or translational control sequence which controls or regulates the expression of a coding sequence in a host cell with a transient fluorescent reporter protein, comprising the steps of:
   a) transfecting cells with an expression vector comprising a DNA sequence that codes for a fluorescent fusion protein comprising a Green Fluorescent Protein (GFP) and a PEST sequence and having a half life of no more than about ten hours, wherein said expression vector contains said transcriptional or translational control sequence that may affect the expression of said fluorescent fusion protein;
   b) treating said transfected cell with said test compound or a control compound that has no effect on the expression of said fluorescent fusion protein; and
   c) detecting an amount of fluorescence in said cells, wherein an increase or decrease in fluorescence in cells treated with said test compound compared to cells treated with said control compound indicates a positive or negative effect respectively of said test compound on the regulatory function of said transcriptional or translational control sequence.

7. The method of claim 6 wherein the GFP is wild type GFP, GFPS65T, humanized GFP, EGFP, blue-emitting GFP, cyan-emitting GFP or yellow-emitting GFP.

8. The method of claim 6 wherein the PEST sequence is selected from the group consisting of a murine ornithine decarboxylase (MODC) PEST sequence, amino acids 376–461 of MODC, amino acids 376–456 of MODC and amino acids 422–461 of MODC.

9. The method of claim 6 wherein the PEST sequence is selected from the group consisting of variants of $MODC_{376-461}$, $MODC_{376-456}$, and $MODC_{422-461}$, containing amino acid substitutions selected from the group consisting of P26A/P427A, P438A, E428A/E430A/E431A, E444A, S440A, S445A, T436A, D433A/D434A and D448A.

* * * * *

SEQUENCE LISTING

<160> NUMBER OF SEQ ID NOS: 14

<210> SEQ ID NO 1
<211> LENGTH: 281
<212> TYPE: PRT
<213> ORGANISM: artificial sequence
<220> FEATURE:
<223> OTHER INFORMATION: Sequence of the EGFP-MODC422-461 fusion protein.

<400> SEQUENCE: 1

```
Met Val Ser Lys Gly Glu Glu Leu Phe Thr Gly Val Val Pro Ile
                 5                  10                  15

Leu Val Glu Leu Asp Gly Asp Val Asn Gly His Lys Phe Ser Val
                20                  25                  30

Ser Gly Glu Gly Glu Gly Asp Ala Thr Tyr Gly Lys Leu Thr Leu
                35                  40                  45

Lys Phe Ile Cys Thr Thr Gly Lys Leu Pro Val Pro Trp Pro Thr
                50                  55                  60

Leu Val Thr Thr Leu Thr Tyr Gly Val Gln Cys Phe Ser Arg Tyr
                65                  70                  75

Pro Asp His Met Lys Gln His Asp Phe Phe Lys Ser Ala Met Pro
                80                  85                  90

Glu Gly Tyr Val Gln Glu Arg Thr Ile Phe Phe Lys Asp Asp Gly
                95                 100                 105

Asn Tyr Lys Thr Arg Ala Glu Val Lys Phe Glu Gly Asp Thr Leu
               110                 115                 120

Val Asn Arg Ile Glu Leu Lys Gly Ile Asp Phe Lys Glu Asp Gly
               125                 130                 135

Asn Ile Leu Gly His Lys Leu Glu Tyr Asn Tyr Asn Ser His Asn
               140                 145                 150

Val Tyr Ile Met Ala Asp Lys Gln Lys Asn Gly Ile Lys Val Asn
               155                 160                 165

Phe Lys Ile Arg His Asn Ile Glu Asp Gly Ser Val Gln Leu Ala
               170                 175                 180

Asp His Tyr Gln Gln Asn Thr Pro Ile Gly Asp Gly Pro Val Leu
               185                 190                 195

Leu Pro Asp Asn His Tyr Leu Ser Thr Gln Ser Ala Leu Ser Lys
               200                 205                 210

Asp Pro Asn Glu Lys Arg Asp His Met Val Leu Leu Glu Phe Val
               215                 220                 225

Thr Ala Ala Gly Ile Thr Leu Gly Met Asp Glu Leu Tyr Lys Lys
               230                 235                 240

Leu Ser His Gly Phe Pro Pro Glu Val Glu Glu Gln Asp Asp Gly
               245                 250                 255

Thr Leu Pro Met Ser Cys Ala Gln Glu Ser Gly Met Asp Arg His
               260                 265                 270

Pro Ala Ala Cys Ala Ser Ala Arg Ile Asn Val
               275                 280
```

<210> SEQ ID NO 2
<211> LENGTH: 850
<212> TYPE: DNA
<213> ORGANISM: artificial sequence
<220> FEATURE:
<223> OTHER INFORMATION: DNA sequence which encodes the EGFP-MODC422-461

-continued

```
        fusion protein.

<400> SEQUENCE: 2
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagaag     720
cttagccatg gcttcccgcc ggaggtggag gagcaggatg atggcacgct gcccatgtct     780
tgtgcccagg agagcgggat ggaccgtcac cctgcagcct gtgcttctgc taggatcaat     840
gtgtagatgc                                                           850

<210> SEQ ID NO 3
<211> LENGTH: 28
<212> TYPE: PRT
<213> ORGANISM: artificial sequence
<220> FEATURE:
<222> LOCATION: 423..450
<223> OTHER INFORMATION: PEST sequence of the C terminus of murine
      ornithine decarboxylase, MODC422-461.

<400> SEQUENCE: 3

His Gly Phe Pro Pro Glu Val Glu Glu Gln Asp Asp Gly Thr Leu
                5                   10                  15

Pro Met Ser Cys Ala Gln Glu Ser Gly Met Asp Arg His
                20                  25

<210> SEQ ID NO 4
<211> LENGTH: 28
<212> TYPE: PRT
<213> ORGANISM: artificial sequence
<220> FEATURE:
<222> LOCATION: 423..450
<223> OTHER INFORMATION: Mutant PEST sequence P426A/P427A of
      MODC422-461.

<400> SEQUENCE: 4

His Gly Phe Ala Ala Glu Val Glu Glu Gln Asp Asp Gly Thr Leu
                5                   10                  15

Pro Met Ser Cys Ala Gln Glu Ser Gly Met Asp Arg His
                20                  25

<210> SEQ ID NO 5
<211> LENGTH: 28
<212> TYPE: PRT
<213> ORGANISM: artificial sequence
<220> FEATURE:
<222> LOCATION: 423..450
<223> OTHER INFORMATION: Mutant PEST sequence P438A of MODC422-461.
```

```
<400> SEQUENCE: 5

His Gly Phe Pro Pro Glu Val Glu Glu Gln Asp Asp Gly Thr Leu
                 5                  10                 15

Ala Met Ser Cys Ala Gln Glu Ser Gly Met Asp Arg His
             20                  25

<210> SEQ ID NO 6
<211> LENGTH: 28
<212> TYPE: PRT
<213> ORGANISM: artificial sequence
<220> FEATURE:
<222> LOCATION: 423..450
<223> OTHER INFORMATION: Mutant PEST sequence E428A/E430A/E431A of
      MODC422-461.

<400> SEQUENCE: 6

His Gly Phe Pro Pro Ala Val Ala Ala Gln Asp Asp Gly Thr Leu
                 5                  10                 15

Pro Met Ser Cys Ala Gln Glu Ser Gly Met Asp Arg His
             20                  25

<210> SEQ ID NO 7
<211> LENGTH: 28
<212> TYPE: PRT
<213> ORGANISM: artificial sequence
<220> FEATURE:
<222> LOCATION: 423..450
<223> OTHER INFORMATION: Mutant PEST sequence E444A of MODC422-461.

<400> SEQUENCE: 7

His Gly Phe Pro Pro Glu Val Glu Glu Gln Asp Asp Gly Thr Leu
                 5                  10                 15

Pro Met Ser Cys Ala Gln Ala Ser Gly Met Asp Arg His
             20                  25

<210> SEQ ID NO 8
<211> LENGTH: 28
<212> TYPE: PRT
<213> ORGANISM: artificial sequence
<220> FEATURE:
<222> LOCATION: 423..450
<223> OTHER INFORMATION: Mutant PEST sequence S440A of MODC422-461.

<400> SEQUENCE: 8

His Gly Phe Pro Pro Glu Val Glu Glu Gln Asp Asp Gly Thr Leu
                 5                  10                 15

Pro Met Ala Cys Ala Gln Glu Ser Gly Met Asp Arg His
             20                  25

<210> SEQ ID NO 9
<211> LENGTH: 28
<212> TYPE: PRT
<213> ORGANISM: artificial sequence
<220> FEATURE:
<222> LOCATION: 423..450
<223> OTHER INFORMATION: Mutant PEST sequence S445A of MODC422-461.

<400> SEQUENCE: 9

His Gly Phe Pro Pro Glu Val Glu Glu Gln Asp Asp Gly Thr Leu
                 5                  10                 15

Pro Met Ser Cys Ala Gln Glu Ala Gly Met Asp Arg His
             20                  25

<210> SEQ ID NO 10
```

```
<211> LENGTH: 28
<212> TYPE: PRT
<213> ORGANISM: artificial sequence
<220> FEATURE:
<222> LOCATION: 423..450
<223> OTHER INFORMATION: Mutant PEST sequence T436A of MODC422-461.

<400> SEQUENCE: 10

His Gly Phe Pro Pro Glu Val Glu Glu Gln Asp Asp Gly Ala Leu
                5                  10                  15
Pro Met Ser Cys Ala Gln Glu Ser Gly Met Asp Arg His
                20                  25

<210> SEQ ID NO 11
<211> LENGTH: 28
<212> TYPE: PRT
<213> ORGANISM: artificial sequence
<220> FEATURE:
<222> LOCATION: 423..450
<223> OTHER INFORMATION: Mutant PEST sequence D433A/D434A of
      MODC422-461.

<400> SEQUENCE: 11

His Gly Phe Pro Pro Glu Val Glu Glu Gln Ala Ala Gly Thr Leu
                5                  10                  15
Pro Met Ser Cys Ala Gln Glu Ser Gly Met Asp Arg His
                20                  25

<210> SEQ ID NO 12
<211> LENGTH: 28
<212> TYPE: PRT
<213> ORGANISM: artificial sequence
<220> FEATURE:
<222> LOCATION: 423..450
<223> OTHER INFORMATION: Mutant PEST sequence D448A of MODC422-461.

<400> SEQUENCE: 12

His Gly Phe Pro Pro Glu Val Glu Glu Gln Asp Asp Gly Thr Leu
                5                  10                  15
Pro Met Ser Cys Ala Gln Glu Ser Gly Met Ala Arg His
                20                  25

<210> SEQ ID NO 13
<211> LENGTH: 28
<212> TYPE: PRT
<213> ORGANISM: artificial sequence
<220> FEATURE:
<222> LOCATION: 423..450
<223> OTHER INFORMATION: Mutant PEST sequence H423A of MODC422-461.

<400> SEQUENCE: 13

Ala Gly Phe Pro Pro Glu Val Glu Glu Gln Asp Asp Gly Thr Leu
                5                  10                  15
Pro Met Ser Cys Ala Gln Glu Ser Gly Met Asp Arg His
                20                  25

<210> SEQ ID NO 14
<211> LENGTH: 28
<212> TYPE: PRT
<213> ORGANISM: artificial sequence
<220> FEATURE:
<222> LOCATION: 423..450
<223> OTHER INFORMATION: Mutant PEST sequence R449A/H450A of
      MODC422-461.

<400> SEQUENCE: 14
```

-continued

```
His Gly Phe Pro Pro Glu Val Glu Glu Gln Asp Asp Gly Thr Leu
                5                   10                  15

Pro Met Ser Cys Ala Gln Glu Ser Gly Met Asp Ala Ala
                20                  25
```